United States Patent
Wessels (10) Patent No.: US 7,693,574 B2
(45) Date of Patent: Apr. 6, 2010

(54) SYSTEM AND METHOD FOR DISCRIMINATING HIGH FREQUENCY ELECTROMAGNETIC INTERFERENCE FROM CARDIAC EVENTS

(75) Inventor: Richard Wessels, Scandia, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 346 days.

(21) Appl. No.: 11/216,886

(22) Filed: Aug. 31, 2005

(65) Prior Publication Data
US 2007/0049995 A1 Mar. 1, 2007

(51) Int. Cl.
A61N 1/37 (2006.01)

(52) U.S. Cl. .......................................................... 607/9
(58) Field of Classification Search .................... 607/9, 607/27; 128/901
See application file for complete search history.

(56) References Cited

U.S. PATENT DOCUMENTS

| | | | |
|---|---|---|---|
| 4,091,818 A * | 5/1978 | Brownlee et al. ............. 607/9 |
| 5,010,887 A | 4/1991 | Thornander |
| 5,101,832 A | 4/1992 | Pritchard et al. |
| 5,336,242 A | 8/1994 | Zadeh |
| 5,431,693 A | 7/1995 | Schroeppel |
| 5,564,420 A | 10/1996 | Nazarian et al. |
| 5,647,379 A * | 7/1997 | Meltzer ...................... 128/897 |
| 5,683,425 A | 11/1997 | Hauptmann |
| 5,687,735 A * | 11/1997 | Forbes et al. ................ 600/509 |
| 5,778,881 A | 7/1998 | Sun et al. |
| 5,817,133 A | 10/1998 | Houben |
| 5,836,980 A | 11/1998 | Legay |
| 5,891,171 A * | 4/1999 | Wickham ..................... 607/4 |
| 6,041,250 A | 3/2000 | dePinto |
| 6,144,881 A | 11/2000 | Hemming et al. |
| 6,324,427 B1 | 11/2001 | Florio |
| 6,329,929 B1 | 12/2001 | Weijand et al. |
| 6,477,404 B1 | 11/2002 | Yonce et al. |
| 6,516,225 B1 | 2/2003 | Florio |
| 6,539,253 B2 | 3/2003 | Thompson et al. |
| 6,567,701 B2 | 5/2003 | Vonk |
| 6,622,042 B1 | 9/2003 | Thacker |
| 6,745,076 B2 | 6/2004 | Wohlgemuth et al. |
| 6,760,615 B2 | 7/2004 | Ferek-Petric |
| 6,788,973 B2 | 9/2004 | Davis et al. |
| 6,819,953 B2 | 11/2004 | Yonce et al. |

(Continued)

Primary Examiner—George R Evanisko
Assistant Examiner—Amanda Patton
(74) Attorney, Agent, or Firm—Faegre & Benson LLP (57) ABSTRACT

A method for discriminating electromagnetic interference from a received signal in an implantable medical device includes identifying a frequency component in the input signal that corresponds to electromagnetic interference. The method further includes passing the physiologic frequency component through a bandpass filter, passing the electromagnetic frequency component through a high pass filter in parallel with the bandpass filter, detecting the electromagnetic frequency component from the high pass filter and using the detected EMI to mitigate one or more effects of the electromagnetic frequency component from the physiologic parameter signal passed by the bandpass filter. An implantable device for detecting a predetermined physiologic event includes an electromagnetic interference (EMI) detection module operable to receive a signal characteristic of a physiologic phenomenon, the received signal comprising a plurality of frequency components, the EMI detection module further operable to output a signal identifying frequency components associated with EMI that is included in the received signal; and a mitigation module operable to use the signal output from the EMI detection module to mitigate one or more effects of the frequency components associated with EMI from the received signal.

13 Claims, 9 Drawing Sheets

U.S. PATENT DOCUMENTS

| | | |
|---|---|---|
| 6,873,870 B2 | 3/2005 | Ferek-Petric |
| 6,892,092 B2 | 5/2005 | Palreddy et al. |
| 6,901,291 B2 | 5/2005 | Stoop et al. |
| 6,917,830 B2 | 7/2005 | Palreddy et al. |
| 6,922,584 B2 | 7/2005 | Wang et al. |
| 7,155,275 B2 * | 12/2006 | Linder et al. ............... 600/509 |

* cited by examiner

SYSTEM AND METHOD FOR DISCRIMINATING HIGH FREQUENCY ELECTROMAGNETIC INTERFERENCE FROM CARDIAC EVENTS

TECHNICAL FIELD

The present invention relates generally to systems and methods for detecting electromagnetic interference (EMI), and more particularly, to systems and methods for discriminating the EMI from cardiac event signals.

BACKGROUND

Medical devices can be implanted in the bodies of patients for various purposes. Some medical devices detect physiologic events and may apply therapy in response to certain events of interest. For example, a cardiac pacemaker can detect a lull in the beating of the patient's heart and apply an electrical pulse to stimulate the heart into beating again. Unfortunately, certain phenomena around the patient can cause the medical device to indicate detection of a physiologic event, when, in fact, the physiologic event has not occurred.

For example, medical pulse generators (PGs), such as implanted defibrillators and cardiac pacemakers may detect signals from a device, such as a cellular phone, that emits electromagnetic energy. This electromagnetic energy may be interpreted by the PG to be a physiologic event, and the PG may respond as if it were valid. Such inappropriate therapy can be uncomfortable or potentially harmful to the patient. Electromagnetic energy from external devices, which is not useful to the device of interest, is referred to as electromagnetic interference (EMI).

Many implanted medical devices include electronic filters to attenuate EMI signals. Such filters typically pass signals in ranges of frequencies that are selected based on analysis and assumptions about the types of physiologic data and noise data that are expected. For example, if the EMI is assumed to be above 10 MHz, a filter may be implemented that removes signals above the 10 MHz frequency. Unfortunately, some EMI falls below 10 MHz and such a filter will not effectively remove the lower frequency EMI. In addition, because EMI can end up in frequency ranges that are relatively close to or identical to frequencies indicative of actual physiologic events of interest, it can be difficult to design filters that are able to consistently filter out only the EMI, without also filtering out legitimate signals indicative of relevant physiologic events.

As society becomes more technologically advanced, the potential for the problems noted above are increasing, rather than decreasing. For example, today many people carry with them devices, such as cell phones and personal digital assistants (PDAs), which can emit EMI at various levels of intensity. In addition, the increasing prevalence of systems such as security scanners that emit EMI, is a concern for patients who live and work around such devices. Such modern devices may increase the occurrence of interaction between such devices and implanted medical devices.

SUMMARY

Embodiments include systems, devices, and methods for discriminating EMI in implantable medical devices to thereby reduce the likelihood of misinterpretation of EMI as relevant physiologic events.

An exemplary method for discriminating electromagnetic interference from a received signal in an implantable medical device includes identifying an electromagnetic frequency component in the input signal that corresponds to electromagnetic interference. The method further includes passing the electromagnetic frequency component through a bandpass filter, passing the electromagnetic frequency component through a high pass filter in parallel with the bandpass filter, detecting the electromagnetic frequency component from the high pass filter and using the detected signal to mitigate one of more undesirable effects of the electromagnetic interference component on the physiologic parameter signal passed by the bandpass filter.

An exemplary implantable device for detecting a predetermined physiologic event includes an electromagnetic interference (EMI) detection module operable to receive a signal characteristic of a physiologic phenomenon, the received signal comprising a plurality of frequency components, the EMI detection module further operable to output a signal identifying frequency components associated with EMI that is included in the received signal; and a mitigation module operable to use the signal output from the EMI detection module to remove the effects of the frequency components associated with EMI from the received signal.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
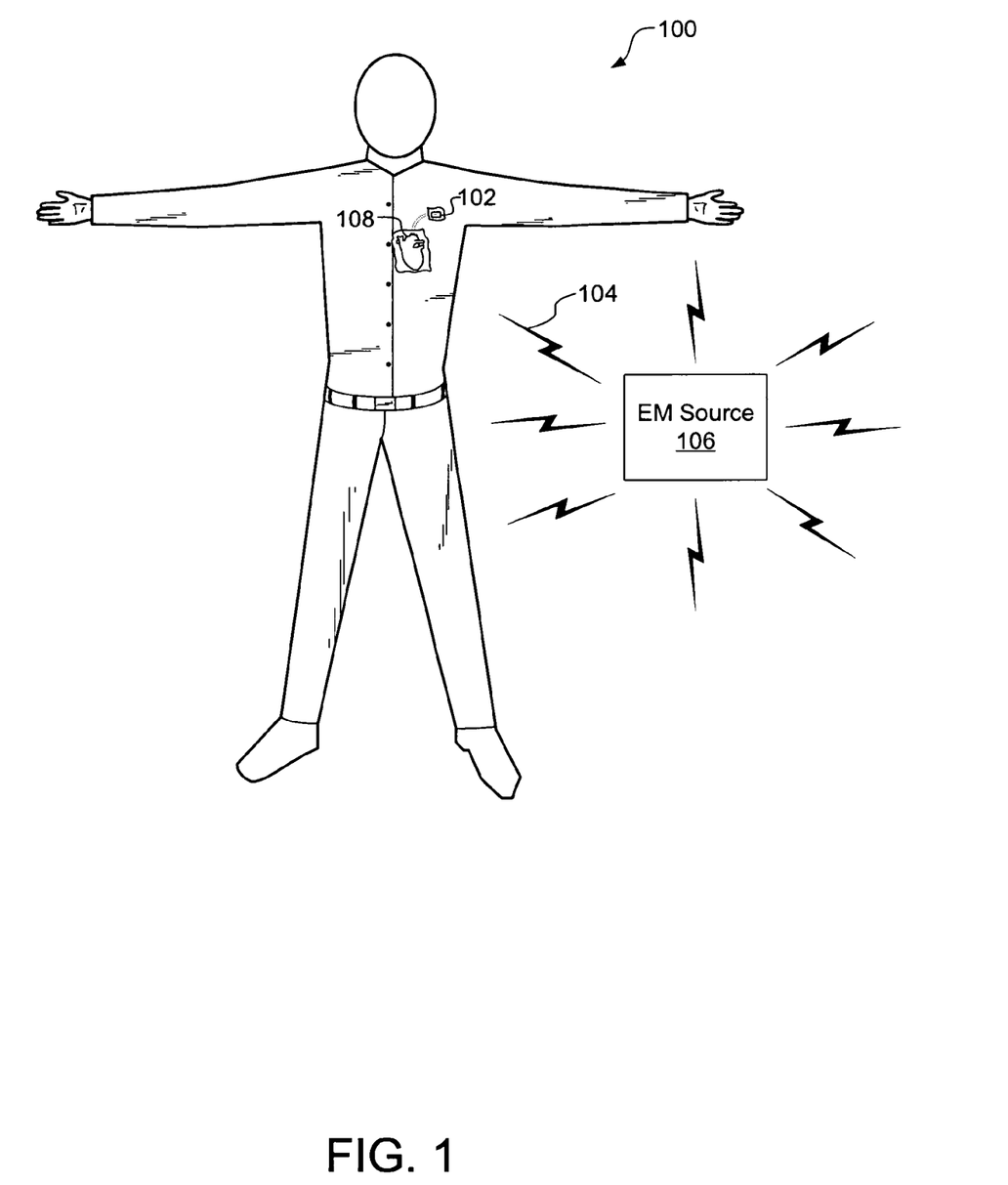
FIG. 1 illustrates a human patient with an implanted pulse generator (PG) that may be affected by electromagnetic interference (EMI) from an EM source.

FIG. 1 illustrates a human patient 100 with an implanted pulse generator (PG) 102 that includes functionality to discriminate electromagnetic interference (EMI) 104 that can arise from one or more EM sources 106. In this particular embodiment, the PG 102 is a cardiac pacemaker 102, although other types of implantable medical devices could also include functionality for discriminating EMI. In general, the purpose of the pacemaker 102 is to detect events in the heart 108 of the patient 100, and administer therapy in response to those detected events. For example, the pacemaker 102 may detect a lull in the beating of the heart 108, and stimulate the heart 108 with an electrical pulse.

Figure 2:
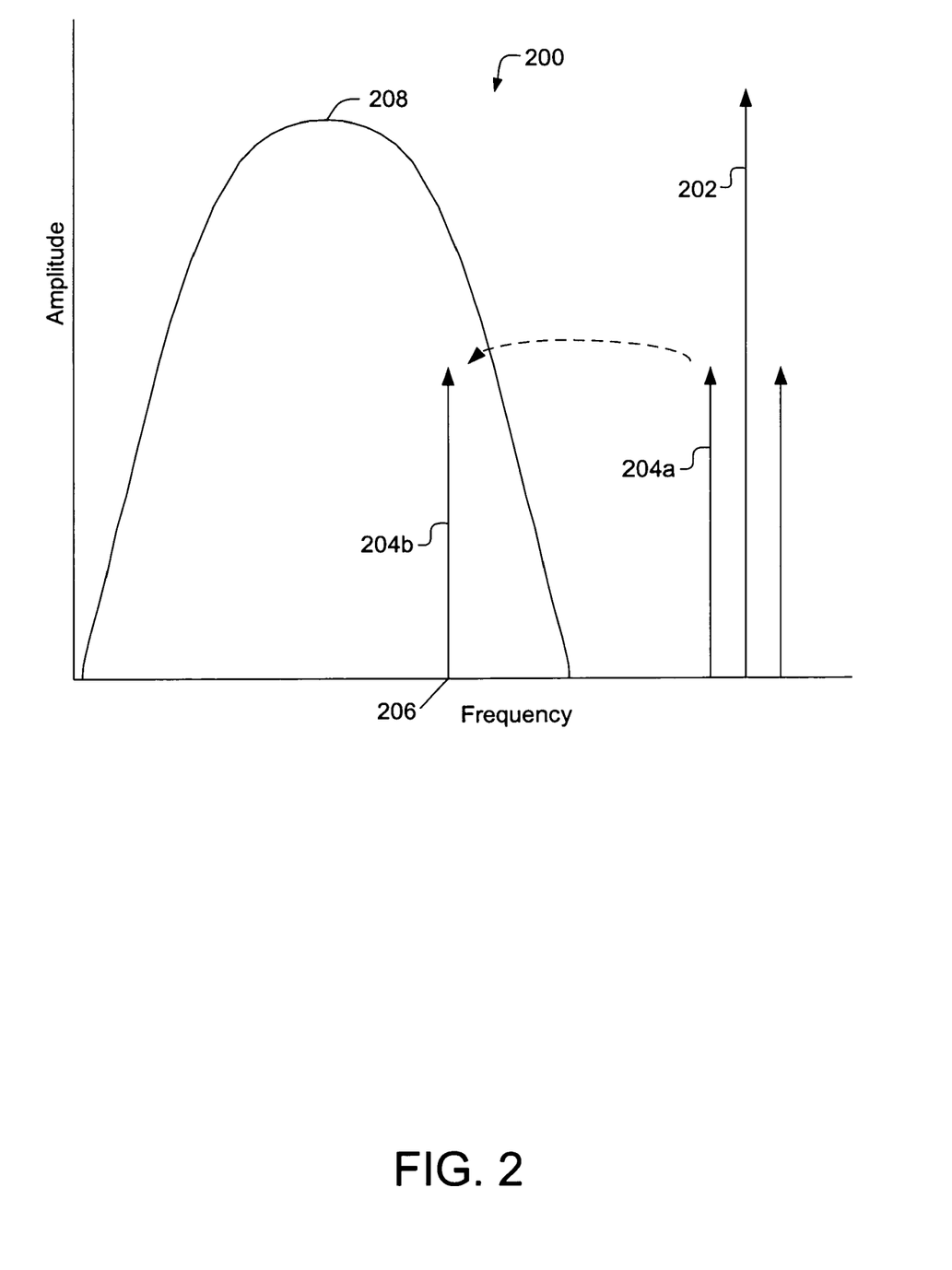
FIG. 2 is a frequency diagram illustrating a situation in which EMI has a frequency component which can be demodulated into the passband of a bandpass filter in an implanted pulse generator.

If the patient 100 goes near an EM source 106, the pacemaker 102 may detect the EMI 104 and mistake the detected EMI 104 for an event in the heart 108. Thus, the pacemaker 102 may stimulate the heart 108 when no stimulation is required or not stimulate the heart 108 when required, potentially causing discomfort or harm to the patient 100. Examples of EM sources 106 include cell phones, welders, ablation processes, cauterizing instruments, theft detectors, security scanners, medical scanners, personal digital assistants and radio frequency identification (RFID) systems. FIG. 2 illustrates how a pacemaker 102 (or other pulse generator) may mistake EMI 104.

FIG. 2 is a frequency diagram 200 illustrating a situation in which EMI 104 from a theft detection device may be mistaken for a cardiac event. EMI 104 occurs at an EM carrier frequency 202 and modulated frequencies 204a. In some embodiments of pulse generators 102, the modulated frequencies 204a may be demodulated down to a lower frequency 206, resulting in a signal 204b with frequency 206 in the passband 208 of the PG 102. Demodulation of the modulated EM frequencies 204a can occur due to PG non-linearities arising from diodes, transistors, or other components.

The spike 204b at lower frequency 206 is included in a passband 208. Passband 208 is a characteristic of a bandpass filter in the PG 102. As is discussed in further detail below, a bandpass filter is used in many embodiments of pulse generators for detecting cardiac events. Signals that are passed by the bandpass filter are typically sensed in the PG as being indicative of cardiac events. Thus, the spike 204b will be detected by the pulse generator as indicating the occurrence of a cardiac event. However, in fact, the spike 204b is not due to a cardiac event, but rather, the spike 204b arises because of the EMI 104.

Figure 3:
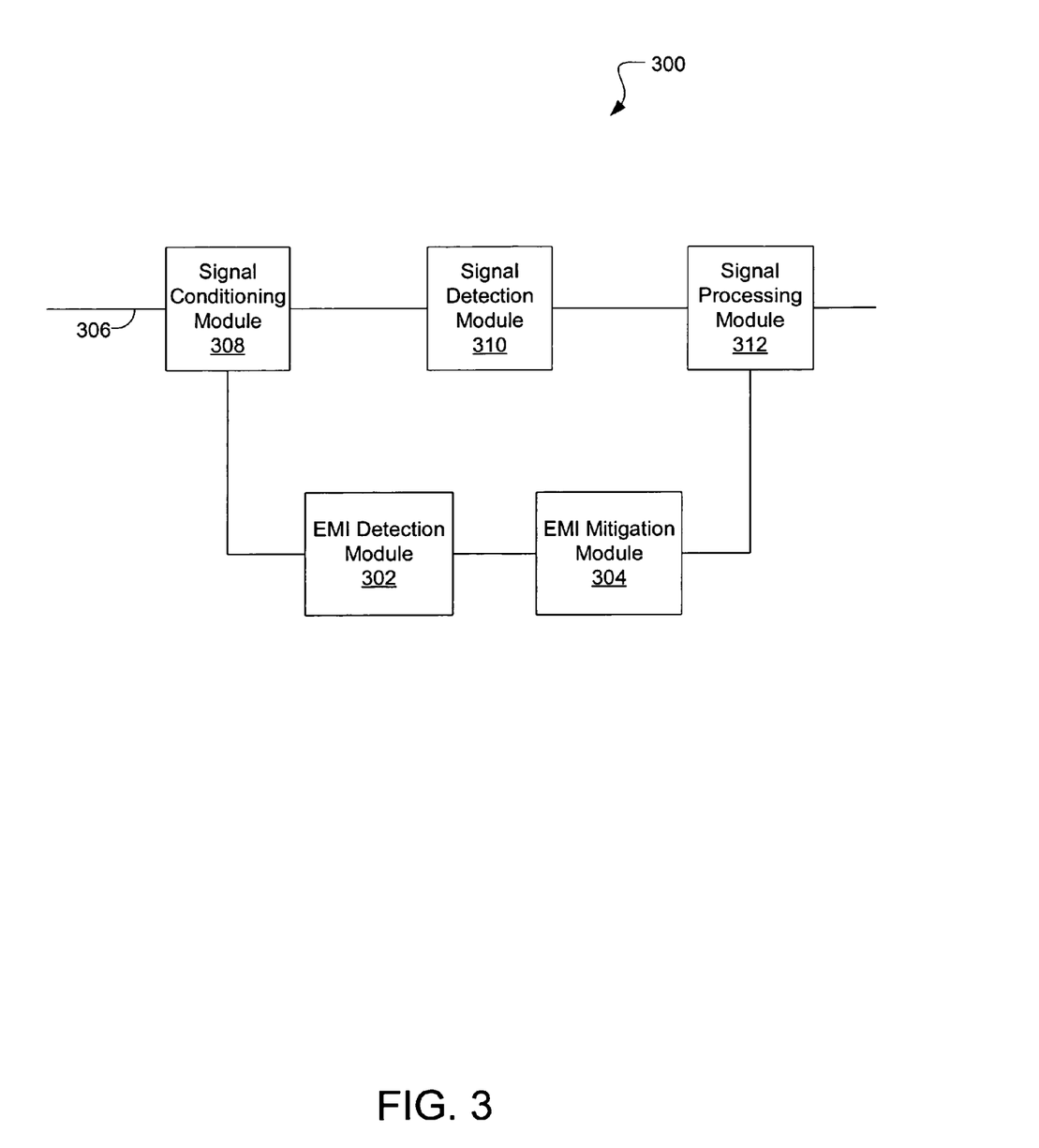
FIG. 3 is a functional block diagram illustrating exemplary components in one embodiment of an implantable PG, including an EMI detection module.

FIG. 3 is a functional block diagram illustrating an embodiment of a physiologic event detection module, such as cardiac event detection module 300, which includes an embodiment of an EMI detection module 302 and EMI mitigation module 304. In this simplified illustration, a signal indicative of a physiologic phenomenon, such as cardiac signal 306, is input into a signal conditioning module 308 of the cardiac event detection module 300. The cardiac signal 306 typically includes multiple frequency components characteristic of associated phenomena. Some frequency components may be those associated with EMI that is included in the cardiac signal 306.

The signal conditioning module 308 typically filters the physiologic parameter signal by passing predetermined frequency components, and attenuating others. Signal conditioning module 308 is generally known to those skilled in the art. A particular embodiment of a signal conditioning module 308 is illustrated in FIG. 4 and discussed in detail below.

Continuing with the upper portion of the cardiac event detection module 300, the output of the signal conditioning module 308 is input into a signal detection module 310. Signal detection module 310 typically includes analog-to-digital conversion and digital signal control, which are generally known to those skilled in the art. Output from the signal detection module 310 is received by a signal processing module 312, which further analyzes the physiologic signal to detect a physiologic event of interest. Particular embodiments of the signal detection module 310 and signal processing module 312 are shown in FIG. 4 and discussed below.

Facilitating the process of physiologic event detection are the EMI detection module 302 and the EMI mitigation module 304. The EMI detection module 302 receives the cardiac signal 306 and identifies frequency components in the cardiac signal 306 that are associated with EMI. Beneficially, the EMI detection module 302 passes the detected EMI frequency components in the output signal. Using the output signal from the EMI detection module, the EMI mitigation module 304 identifies and/or removes EMI frequency components from the cardiac signal 306 at the upper portion of the detection module 300. Particular embodiments of the EMI detection module 302 and the EMI mitigation module 304 are illustrated in FIG. 4 and discussed in further detail below.

Figure 4:
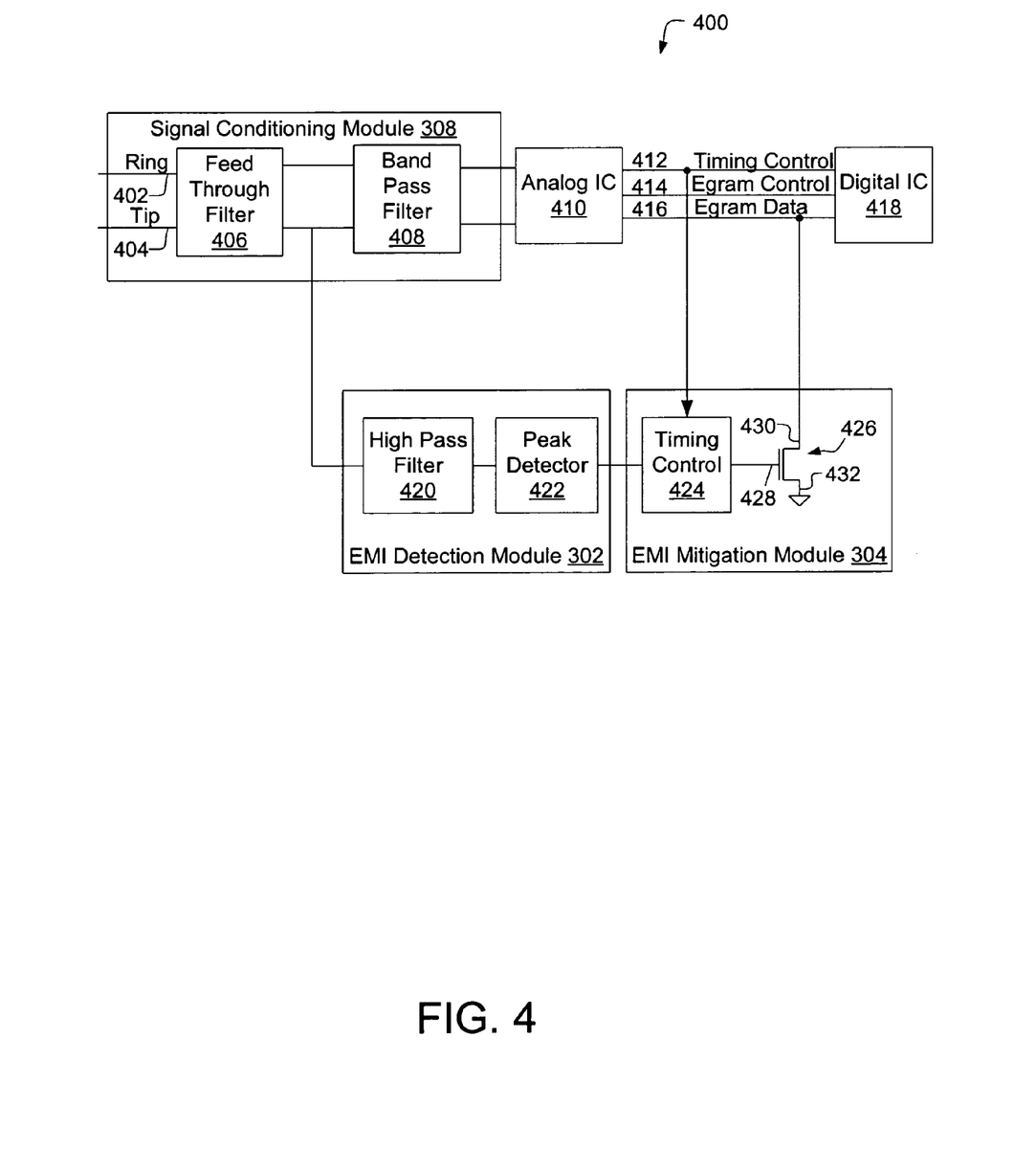
FIG. 4 is another functional block diagram illustrating exemplary components in another embodiment of an implantable PG, including an EMI detection module.

FIG. 4 is another functional block diagram illustrating exemplary components in another embodiment of an implantable PG 102, which includes EMI detection functionality. In this embodiment, the physiologic signal is composed of two parts: ring 402 and tip 404. Ring 402 and tip 404 are signals received from corresponding leads from the PG 102.

In the illustrated embodiment, signal conditioning module 308 includes a feed through filter (FTF) 406 and a band pass filter (BPF) 408. The FTF 406 attenuates signals at frequencies above a specified cutoff frequency, such as, but not limited to, around 10 MHz, but allows lower frequencies to pass. Although the conventional purpose of the FTF 406 is to filter out EMI frequency components, typical FTF 406 cutoff frequencies are often higher than frequencies of many types of EMI. Thus, the FTF 406 can, and often does, allow EMI frequencies to pass. The output of the FTF 406 is input into BPF 408.

The BPF 408 passes signal components in a range of frequencies (the passband) bounded by an upper cutoff frequency and a lower cutoff frequency. The upper cutoff frequency and the lower cutoff frequency are selected such that frequencies associated with cardiac events are included in the passband. However, as discussed above, sometimes frequency components associated with EMI sources are included in the passband, through either direct content or through demodulation of modulated high frequency electromagnetic signals. The EMI detection module 302 identifies such high frequency EMI signals and enables them to be mitigated either by removal from the cardiac signal or by identifying them and removing their effect from the resulting therapy.

The output of the BPF 408 is input into an analog IC 410 that performs signal conversion, detection, and/or control processing. In the illustrated embodiment, the output of the analog IC 410 is a timing control signal 412, an electrocardiogram data (egram) signal 416, and an egram control signal 414. Analog ICs 410 to produce such signals are known to those skilled in the art. A digital IC 418 receives the timing control signal 412, electrocardiogram data (egram) signal 416, and egram control signal 414 and performs signal processing to detect a physiologic (e.g., cardiac) event of interest. The egram data signal 416 is a digital representation of the ring 402 and/or tip 404 signals. The output of the digital IC 418 indicates whether a cardiac event of interest has occurred and can be used to trigger administration of therapy.

Acting in parallel with the signal conditioning module 308, the analog IC 410 and the digital IC 418 are the EMI detection module 302 and the EMI mitigation module 304. In this particular embodiment, the tip signal 404 is input into the EMI detection module 302 because the tip signal 404 is typically the larger of the two signals. In other embodiments, the ring signal 402 may also be input into the EMI detection module 302 for use in the process of detecting and discriminating EMI.

In the embodiment of FIG. 4, the EMI detection module 302 includes a high pass filter (HPF) 420 and a peak detector 422. HPF 420 passes frequency components above a specified cutoff frequency. The specified cutoff frequency is selected to include expected EMI frequencies without including a significant amount of the cardiac signal content. The HPF 420 cutoff frequency can be lower than the upper cutoff frequency of the BPF 408. By way of example, but not limitation, the HPF 420 cutoff frequency may be set to around 1 KHz. As such, the HPF 420 will block most frequency components associated with relevant physiologic phenomena, but all frequency components associated with EMI above 1 kHz would pass.

Figure 6:
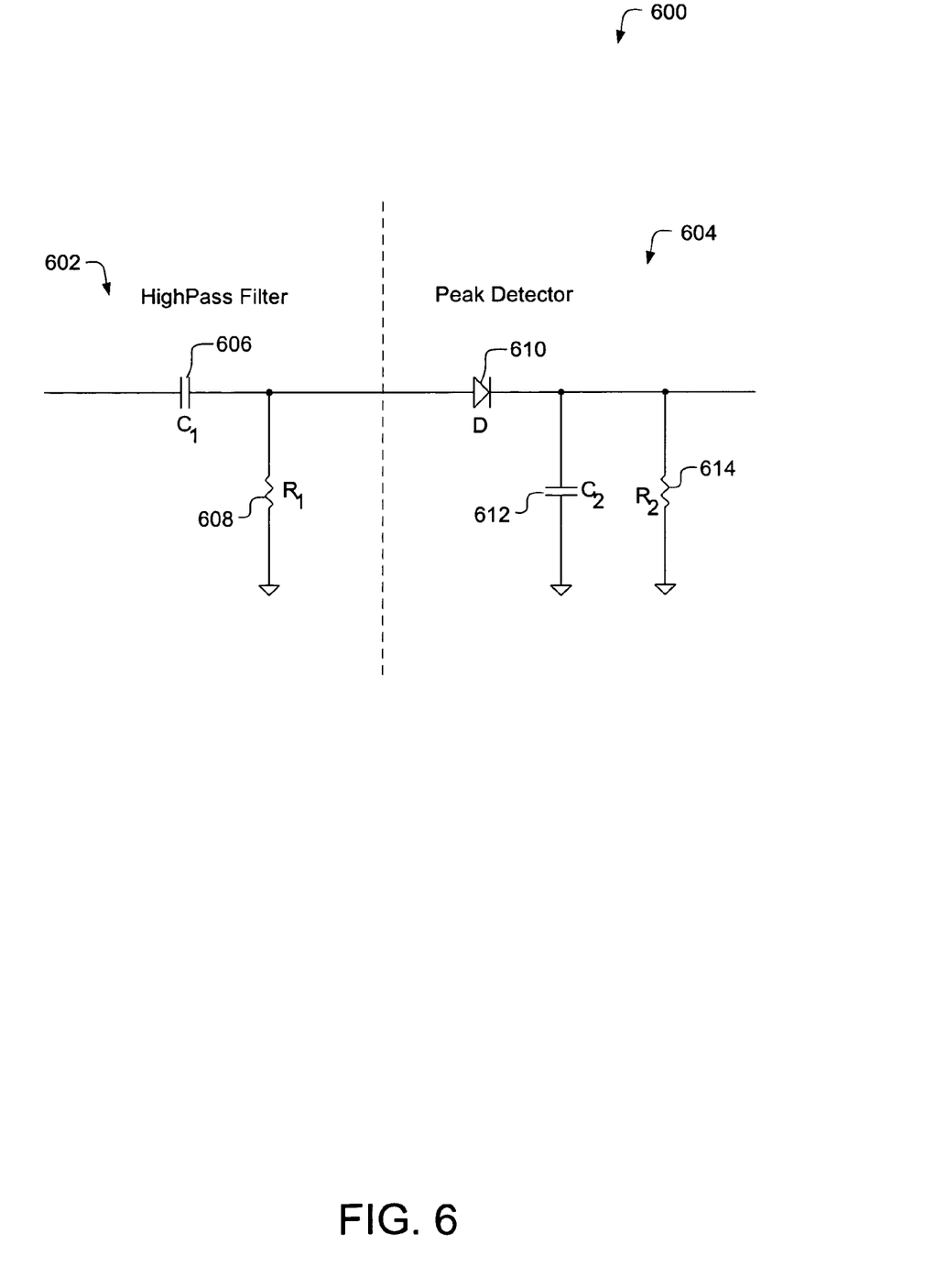
FIG. 6 is a circuit diagram illustrating exemplary embodiments of a high-pass filter and a peak detector that may be used in an EMI detection module, such as the one shown in FIG. 4.

The EMI detection module 302 also includes the peak detector 422, which measures voltage and stores the voltage for a time duration. The time duration is determined by design parameters. Exemplary embodiments of an HPF 420 and a peak detector 422 are shown in FIG. 6 and discussed in detail below. The peak detector 422 captures peaks of the signals that are passed by the HPF 420, thereby identifying the maximum values associated with EMI frequencies. These peaks can be used by the EMI mitigation module 304 to remove the EMI or the resulting effects of the EMI from the cardiac signal that is input to the digital IC 418, to reduce the likelihood that the digital IC 418 will interpret extraneous noise as a physiologic event of interest.

Figure 8:
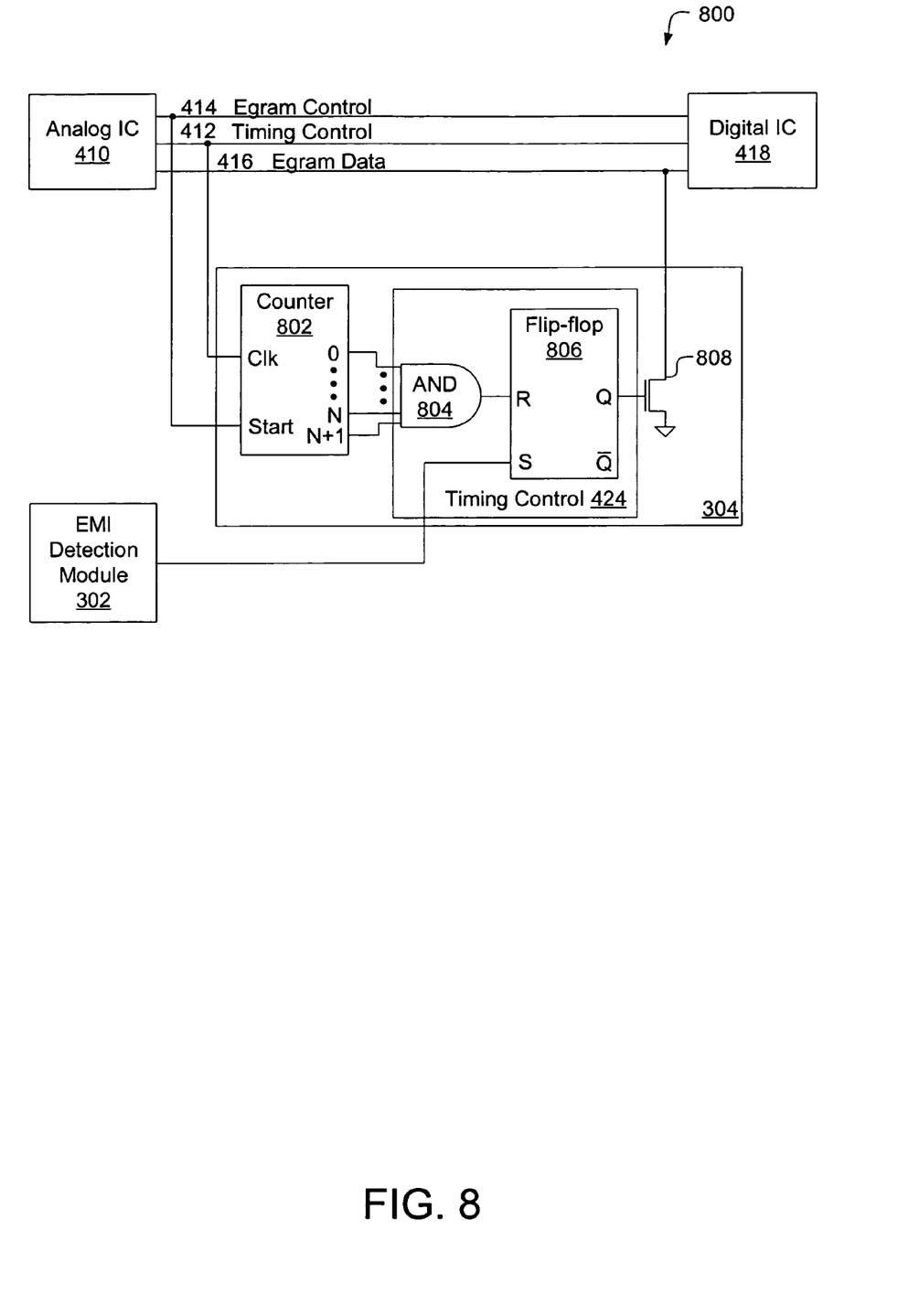
FIG. 8 is a digital circuit diagram depicting function of exemplary circuits associated with the functional diagram shown in FIG. 4.

The illustrated embodiment of the EMI mitigation module 304 includes timing and control module 424 and a field effect transistor (FET) 426. This embodiment of the EMI mitigation module 304 is simplified for purposes of illustration. FIG. 8 illustrates control, and mitigation circuitry that could be used in an EMI mitigation module according to another embodiment.

In another embodiment (not shown), the mitigation module 304 can include the digital IC 418.

In the embodiment of FIG. 4, timing control module 424 receives the timing control signal 412 from the analog IC 410 and uses the timing control signal 412 to synchronize the output of the peak detector 422 with the egram signal 416. At appropriate times, the timing control module 424 passes the output of the peak detector 422. The output of the timing control module 424 is connected to a gate electrode 428 of the FET 426. Thus, at controlled times the signal from the peak detector can cause the channel of the FET 426 to conduct, creating a short circuit from the source electrode 432 to the drain electrode 430.

As illustrated in this embodiment, the drain electrode 430 is connected to the egram signal 416 and the source electrode 432 is connected to ground. In this configuration, when the voltage at the gate electrode 428 reaches a threshold voltage, the drain electrode 430 will become grounded via the source electrode 432. As such, the egram signal 416 will become grounded when EMI frequency components are detected by the EMI detection module 302.

The term "module" as used herein refers to a functional component that can be implemented in hardware, software, firmware or any combination of hardware, software, or firmware. In embodiments that include software, the software typically includes data and instructions that are readable and executable by a processor, such as a microprocessor, microcontroller, or digital signal processor. Firmware may include data in, for example, a programmable read only memory (PROM), which incorporates functional design parameters.

Figure 5:
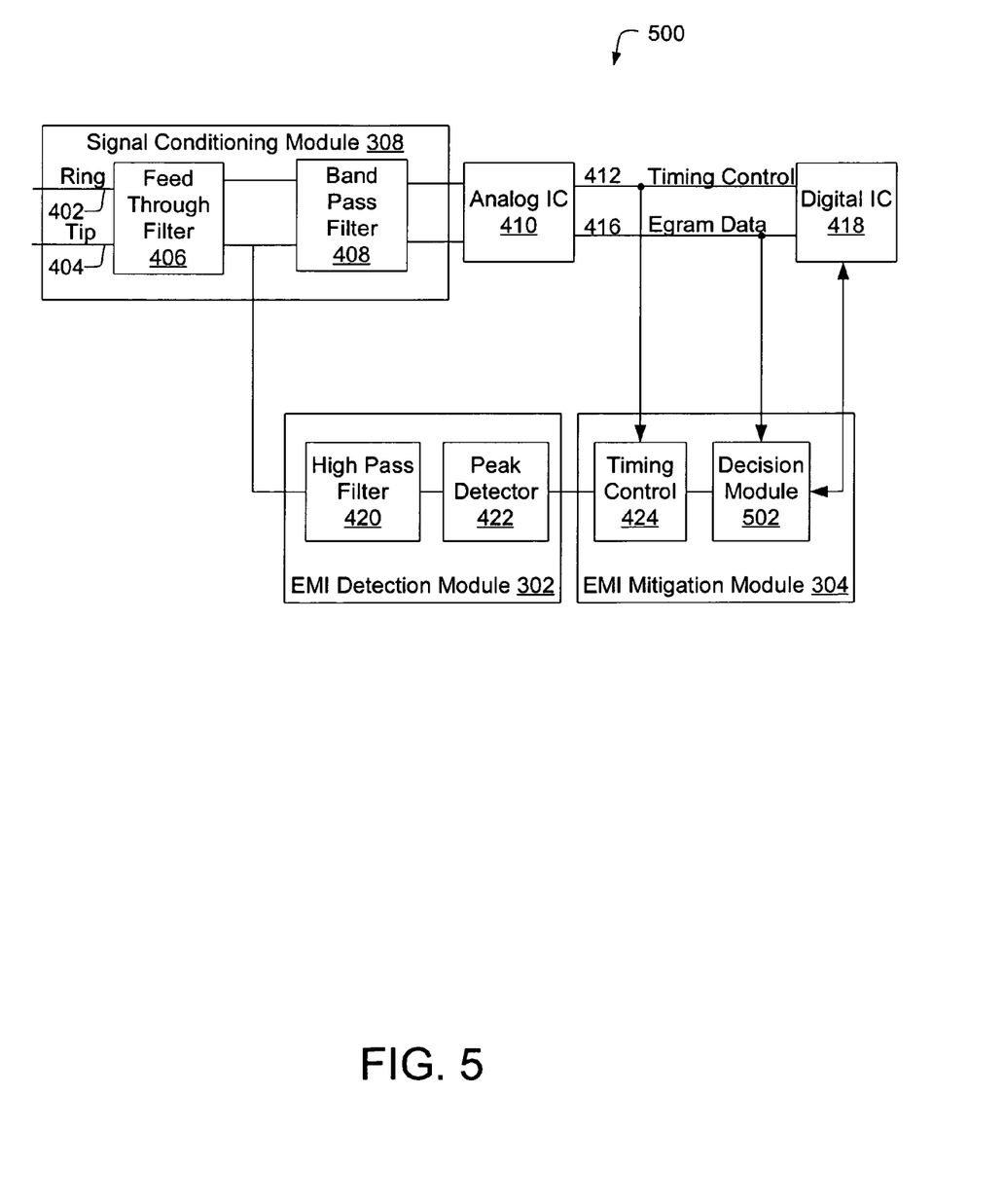
FIG. 5 is another functional block diagram illustrating exemplary components in another embodiment of a system for detecting and mitigating EMI in an implantable PG.

FIG. 5 is another functional block diagram 500 illustrating exemplary components in another embodiment of an implantable PG 102, which includes EMI detection functionality. This embodiment is generally similar to the embodiment shown in FIG. 4, with the exception of different components included in the EMI mitigation module 304.

In the embodiment of FIG. 5, the EMI mitigation module 304 includes a decision module 502, which could be an arrangement of active and/or passive components that use the egram data 416 to generate a signal that can be used by the digital IC 418 to remove or mitigate effects of EMI on cardiac data. In one embodiment, the decision module 502 determines which portions of the egram data include EMI data and mark, or tag those portions in the output to the digital IC 418. In another embodiment, the decision module 502 removes EMI from the cardiac signal. This removal, or mitigation, of EMI can occur in a number of ways. By way of example, but not limitation, the analog signal passed by the bandpass filter could be attenuated to a point where the amplitude of the EMI would not influence the operation of the device. The digitally converted physiologic signal could have the digital data representing the EMI portion of the signal flagged by setting a specific bit in the digital word. The device processor (e.g., in digital IC 418) could then deal with the flagged EMI data by ignoring it, attenuating it, filtering it with digital means or a number of other actions.

FIG. 6 is a circuit diagram illustrating exemplary embodiments of a simplified high-pass filter 602 and peak detector 604 that may be used in an EMI detection module 302, such as the one shown in FIG. 4. The exemplary high-pass filter 602 includes a capacitor, $C_1$ 606, and a resistor, $R_1$ 608. In this simplified HPF 602, the time constant of the filter is given by $C_1$ multiplied by $R_1$, and the corresponding cutoff frequency can be selected according to $1/(R_1 C_1)$.

Turning to the peak detector 604, a diode D 610 passes current to a capacitor $C_2$ 612 in parallel with a resistor $R_2$ 614. The time constant associated with $C_2$ 612 and $R_2$ 614 is generally slower than the frequency of the signal output by the HPF 602. Each cycle of EMI output by the HPF 602 causes the capacitor $C_2$ to charge, until $C_2$ reaches a predetermined peak voltage value. After charging, capacitor $C_2$ 612 discharges via resistor $R_2$ 614, while no EMI is input to the peak detector 604. The functions of $C_2$ and $R_2$ can be implemented using other means including but not limited to FETs, BJTs and switched cap circuits.

Figure 7:
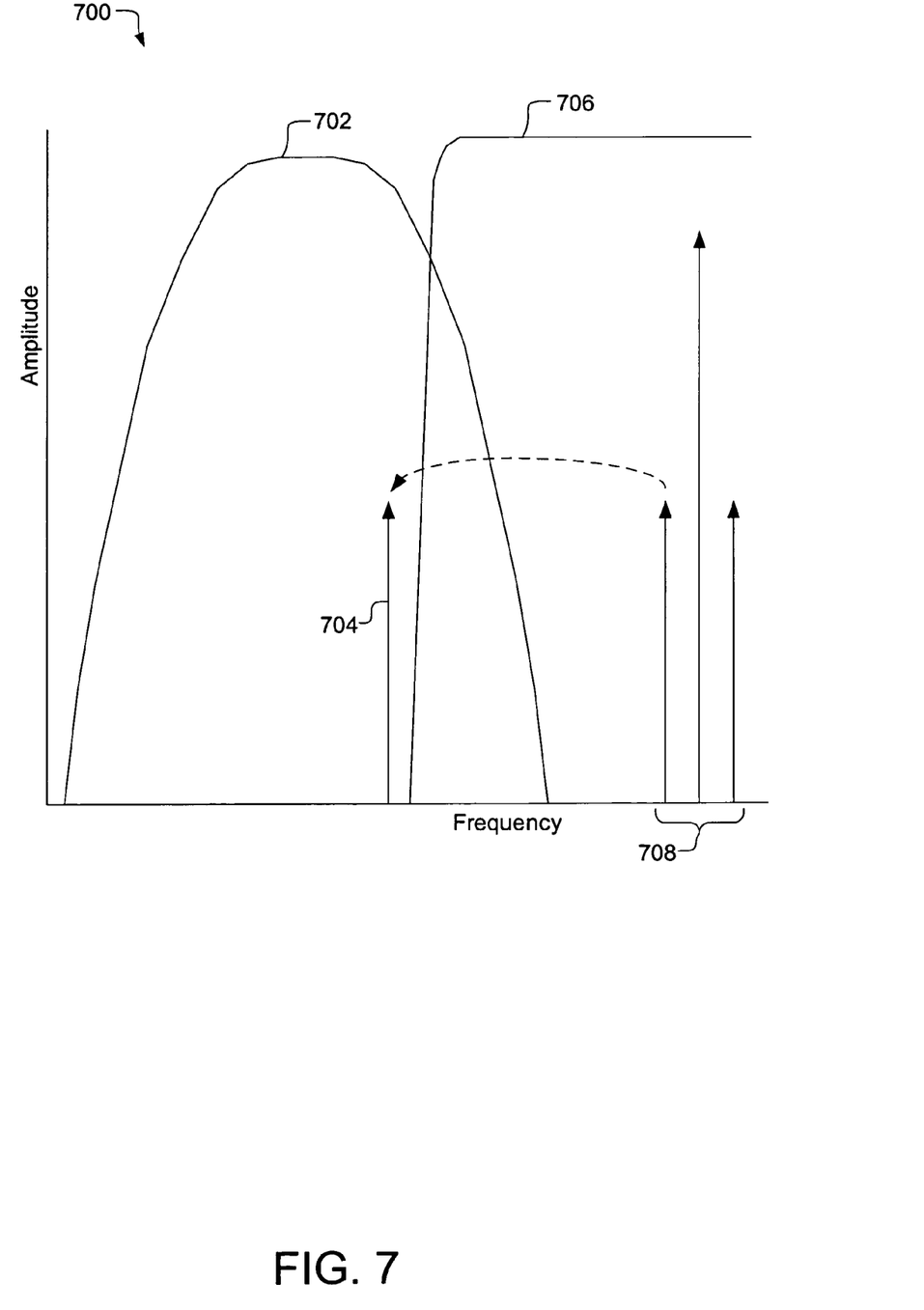
FIG. 7 is a frequency diagram illustrating an exemplary embodiment of bandpass filter and highpass filter characteristics that may be used in a conditioning and mitigation module, such as the one shown in FIG. 4.

FIG. 7 is an exemplary frequency diagram 700 illustrating frequency responses of a bandpass filter 702 (e.g., BPF 408, FIG. 4) and a high pass filter 706 (e.g., HPF 420, FIG. 4). A passband 702 of a bandpass filter includes a frequency component 704 caused by demodulated EMI 708. A high pass filter passband 706 is designed to pass the EMI for mitigation and therefore eliminating the effects of the EMI component 704.

FIG. 8 illustrates an exemplary embodiment of an EMI mitigation circuit 800. The mitigation circuit 800 is disposed between EMI detection module 302 and analog IC 410 on one side, and digital IC 418 on the other.

The illustrated embodiment of the mitigation circuit 800 includes a counter 802 that uses egram control 414 to increment through each frame of data transmitted from the analog IC 410. Egram control 414 is connected to start line of the counter 802. Input to the clock line of the counter is connected to timing control signal 412 output from the analog IC 410. In one embodiment, the clock frequency input to the clock line of the counter is 32 KHz. In this embodiment, the counter 802 does not roll over, but stops at full count.

The set line of the flip-flop 806 is connected to the output of the EMI detection module 302. As such, when an EMI peak is detected and output to the flip-flop 806, flip-flop 806 output line Q is set; when counter 802 reaches the appropriate count, the output line Q is reset. The output line Q is connected to the gate of FET 808, which grounds egram data signal 416 when the output Q of the flip-flop 806 is set. This results in an indication that EMI is present during the time when Q is set. The determination of proper count from counter 802 is determined by AND gate 804 which receives the output bits of the counter 802. When the appropriate output bits of the counter 802 are set as a result of the required count being reached, the AND gate 804 sets its output. The output of the AND gate 804 is connected to a reset line of an R-S flip-flop 806.

Figure 9:
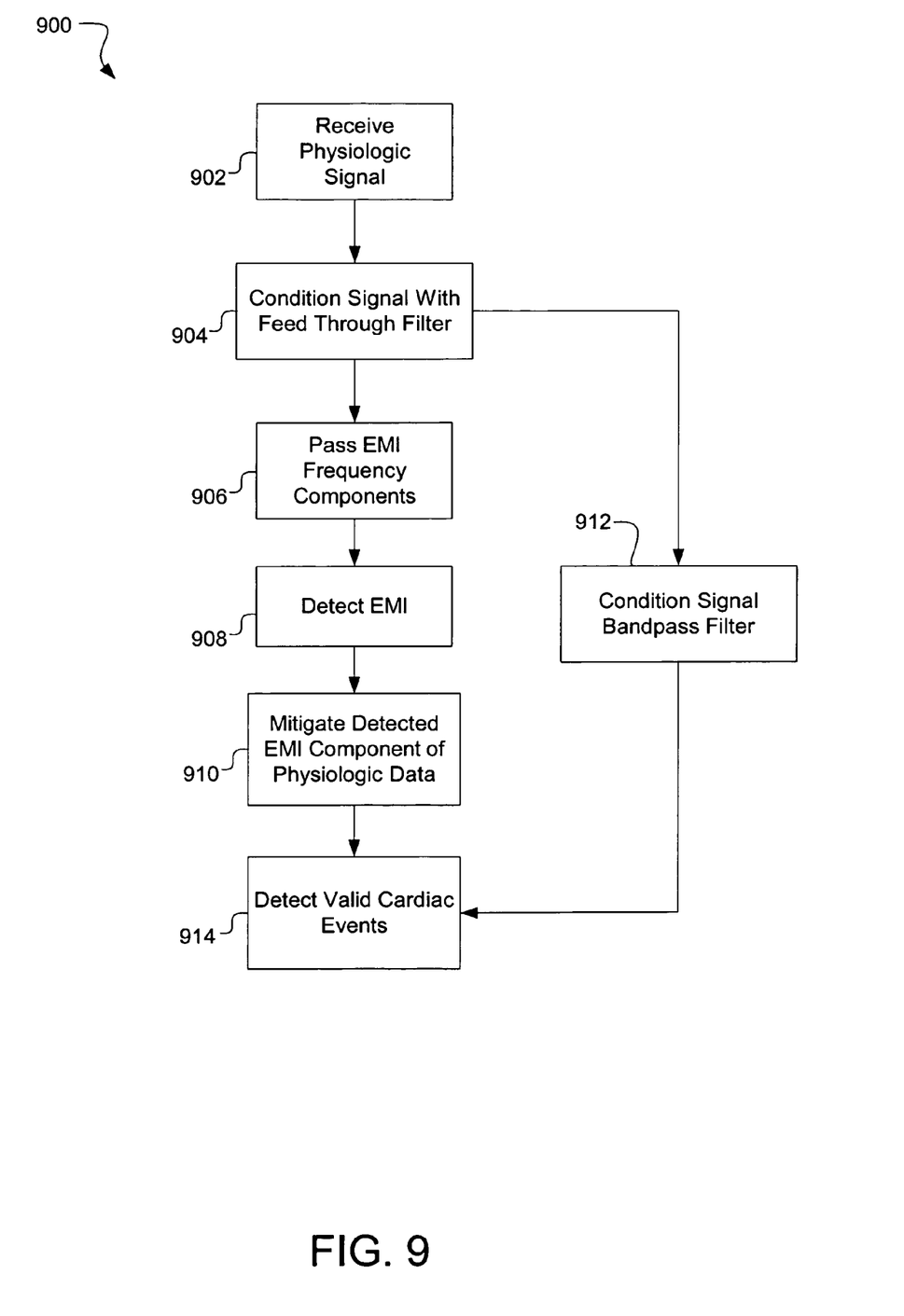
FIG. 9 is a flowchart illustrating exemplary operations in accordance with one embodiment of an algorithm that can be carried out by some embodiments of an implantable PG for detecting and mitigating EMI.

FIG. 9 is a flowchart illustrating exemplary operations in accordance with one embodiment of an EMI detection algorithm 900. The EMI detection algorithm can be carried out by an implantable medical device, such as a pulse generator (PG), or other therapy administering device.

A receiving operation 902 receives a signal based on a physiologic parameter of interest. In one embodiment, the receiving operation 902 receives an electrical cardiac signal from a patient's heart. The receiving operation 902 may receive other types of physiological parameters. The signal may include unwanted EMI emitted from an EMI source, such as a security alarm system. The signal received includes multiple frequency components characteristic of the physiological phenomenon as well as the EMI.

A conditioning operation 904 filters the received signal with a feed through filter and a second conditioning operation 912 with band pass filtering. In one embodiment, the feed through filter passes all frequency components that are less than 10 MHz, and the bandpass filter passes frequency components in a range from 10 Hz to 1 KHz.

A passing operation 906 receives the physiologic signal and passes only high frequency EMI. In one embodiment, the passing operation 906 receives the signal after the feed through filter. A detecting operation 908 analyzes the frequency components passed through the passing operation 906 and indicates when high frequency EMI is detected.

When high frequency EMI is detected, a mitigation operation 910 removes the effects of the EMI from the output from the bandpass filter, based on the detected EMI. These effects on therapy by EMI include but are not limited to increased therapy rate due to tracking, inhibition of required therapy, inappropriate therapy and others. Such undesirable effects can be prevented by identifying, marking, or tagging incoming data that relates to EMI, which could cause those effects, and selectively mitigating or preventing those effects using various techniques.

In one embodiment, mitigating operation 910 selectively mitigates effects of EMI. Selective mitigation may involve synchronizing the detected EMI with the output of the bandpass filter, such that the effect of the EMI in the output from the bandpass filter is eliminated at the proper time, through either attenuation, digital filtering, subtraction or similar functions. In one embodiment, a digital IC, such as digital IC 418, can be employed to eliminate the effect of EMI at the proper time.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. An implantable device for detecting a physiologic event, the device comprising:

an electromagnetic interference (EMI) detection module operable to receive an input signal characteristic of the physiologic event, the input signal including physiologic event components and EMI components, the EMI components including high frequency EMI components, and the EMI detection module being further operable to attenuate the physiologic event components and to pass the high frequency EMI components in an output signal; and a signal conditioning module operable to generate a filtered signal from the input signal, the filtered signal having the high frequency EMI components removed; and a mitigation module operable to use the high frequency EMI components in the output signal from the EMI detection module to remove the EMI components from the filtered signal.

2. The implantable device recited in claim 1, wherein the signal conditioning module includes a bandpass filter having an upper cutoff frequency and a lower cutoff frequency, the bandpass filter operable to receive the input signal, and output a range of frequency components including at least a portion of the EMI components, and wherein the implantable device further comprises:

a timing module operable to synchronize the output signal with the frequency components passed by the bandpass filter, wherein the EMI detection module includes a high pass filter, the high pass filter having a cutoff frequency that is lower than the upper cutoff frequency of the bandpass filter.

3. The implantable device recited in claim 2, further comprising a data processor adapted to generate electrocardiogram (egram) data and timing control data based on output from the bandpass filter, wherein the mitigation module comprises the timing module, and further comprises a decision module, which generates tagged EMI data based on output from the detection module, the egram data, and timing control data, and wherein the tagged EMI data is used to mitigate the effects of the EMI.

4. The implantable device recited in claim 2 wherein the timing module comprises a counter counting packets in frames of data in the signal and setting a flip-flop when a maximum number of packets is counted.

5. The implantable medical device as recited in claim 2, wherein the signal conditioning module includes a feedthrough filter for filtering the frequency components of the received signal prior to being filtered by the bandpass filter, and further wherein the frequency components of the received signal directed to the EMI detection module are filtered by the feedthrough filter but bypass the bandpass filter.

6. An implantable medical device for administering therapy in a body of a patient in response to detecting a physiologic event of interest, the device comprising:
   a physiologic event detection module for receiving an input signal composed of a plurality of frequency components including physiologic event components and EMI components, the physiologic event detection module comprising:
      a bandpass filter for passing the frequency components that are between an upper cutoff frequency and a lower cutoff frequency;
      an electromagnetic interference (EMI) detection module for attenuating the physiologic event components and for passing high frequency components characteristic of the EMI components, wherein the high frequency components have a frequency of at least around 1 kHz; and
      a mitigation module for using the high frequency components characteristic of the EMI component from the EMI detection module to remove the EMI components from the frequency components passed by the bandpass filter, thereby enabling detection of the physiologic event.

7. The implantable medical device as recited in claim 6 wherein the mitigation module comprises a timing control module and a decision module operable to identify one or more frequency components associated with EMI.

8. The implantable medical device as recited in claim 6 wherein the EMI detection module comprises a high pass filter and a peak detector.

9. The implantable medical device as recited in claim 6 wherein the physiologic event detection module further comprises a timing and control module operable to synchronize frequency components passed by the EMI detection module with frequency components passed by the bandpass filter.

10. The implantable medical device as recited in claim 6 further comprising a therapy administration component receiving output from the physiologic event detection module and responsively administering therapy.

11. The implantable medical device as recited in claim 10 wherein the therapy administration component comprises a pulse generator.

12. The implantable medical device as recited in claim 10 wherein the therapy administration component comprises a defibrillator.

13. The implantable medical device as recited in claim 10 wherein the effects of the frequency components passed by the bandpass filter that are characteristic of EMI are selected from a group comprising: increased therapy rate, inhibition of required therapy, and inappropriate therapy.

* * * * *